(12) United States Patent
Weber et al.

(10) Patent No.: US 11,583,258 B2
(45) Date of Patent: Feb. 21, 2023

(54) ULTRASOUND PROCESSING UNIT AND METHOD, AND IMAGING SYSTEM

(71) Applicant: KONINKLIJKE PHILIPS N.V., Eindhoven (NL)

(72) Inventors: Frank Michael Weber, Hamburg (DE); Tilman Wekel, Krummesse (DE); Balasundar Iyyavu Raju, North Andover, MA (US); Jonathan Thomas Sutton, Boston, MA (US); Peter Bingley, Mierlo (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 137 days.

(21) Appl. No.: 17/048,136

(22) PCT Filed: Apr. 9, 2019

(86) PCT No.: PCT/EP2019/058865
§ 371 (c)(1),
(2) Date: Oct. 16, 2020

(87) PCT Pub. No.: WO2019/201655
PCT Pub. Date: Oct. 24, 2019

(65) Prior Publication Data
US 2021/0145413 A1    May 20, 2021

Related U.S. Application Data

(60) Provisional application No. 62/658,942, filed on Apr. 17, 2018.

(30) Foreign Application Priority Data

May 15, 2018  (EP) .................................... 18172400

(51) Int. Cl.
  *A61B 8/00*     (2006.01)
  *G06T 7/246*    (2017.01)
  *A61B 8/08*     (2006.01)

(52) U.S. Cl.
  CPC ................ *A61B 8/54* (2013.01); *A61B 8/085* (2013.01); *A61B 8/0883* (2013.01); *A61B 8/42* (2013.01);
  (Continued)

(58) Field of Classification Search
  CPC ......... A61B 8/54; A61B 8/085; A61B 8/0883; A61B 8/42; A61B 8/5223; A61B 8/5246;
  (Continued)

(56) References Cited

U.S. PATENT DOCUMENTS 5,997,479 A   12/1999  Savord et al.
6,013,032 A    1/2000  Savord
(Continued)

FOREIGN PATENT DOCUMENTS

WO    2017108667 A1    6/2017

OTHER PUBLICATIONS

International Search Report and Written Opinion for International Application No. PCT/EP2019/058865, filed Apr. 9, 2019, 16 pages.
(Continued)

*Primary Examiner* — Boniface Ngathi N
*Assistant Examiner* — Zainab Mohammed Aldarraji (57) ABSTRACT

The invention provides an ultrasound processing unit. A controller (18) of the unit is adapted to receive ultrasound data of an anatomical region, for example of the heart. The controller processes the ultrasound data over a period of time to monitor and detect whether alignment of a particular anatomical feature (34) represented in the data relative to a field of view (36) of the transducer unit is changing over time. In the event that the alignment is changing, the
(Continued)

controller generates an output signal for communicating this to a user, allowing a user to be alerted at an early stage to likelihood of misalignment and loss of imaging or measurement capability.

14 Claims, 3 Drawing Sheets

(52) U.S. Cl.
CPC ............ *A61B 8/5223* (2013.01); *G06T 7/246* (2017.01); *G06T 2207/10132* (2013.01); *G06T 2207/30048* (2013.01)

(58) Field of Classification Search
CPC .. A61B 8/52; A61B 8/483; A61B 8/46; A61B 8/12; A61B 8/5276; G06T 7/246; G06T 2207/10132; G06T 2207/30048; G06T 2207/10136; G06T 2207/20081; G06T 2207/20084
See application file for complete search history.

(56) References Cited

U.S. PATENT DOCUMENTS

| | | |
|---|---|---|
| 6,152,878 A | 11/2000 | Nachtomy et al. |
| 6,623,432 B2 | 9/2003 | Powers et al. |
| 2009/0149756 A1 | 6/2009 | Soler et al. |
| 2011/0262018 A1 | 10/2011 | Kumar et al. |
| 2012/0071758 A1 | 3/2012 | Lachaine et al. |
| 2014/0031688 A1 | 1/2014 | Perrey et al. |
| 2014/0213904 A1 | 7/2014 | Chen et al. |
| 2014/0243671 A1 | 8/2014 | Holl et al. |
| 2015/0011886 A1 | 1/2015 | Radulescu et al. |
| 2017/0105700 A1* | 4/2017 | Bar-Zion ............. A61B 8/0891 |
| 2017/0196540 A1 | 7/2017 | Dufour et al. |
| 2017/0273669 A1 | 9/2017 | Schneider |

OTHER PUBLICATIONS

Omari, et al., "Preliminary results on the feasiblity of using ultrasound to monitor intrafractional motion during radiation therapy for pancreatic cancer", Medical Physics, Aug. 31, 2016, vol. 43, No. 9, pp. 5252-5260.

Jenne, et al., "Ultrasound motion tracking for radiation therapy", vol. 55, No. 11, Oct. 5, 2015, pp. 984-991.

Ecabert, et al., "Automatic Model-Based Segmentation of the Heart in CT Images Medical Imaging", IEEE Transactions on Medical Imaging, Sep. 2008, vol. 27, Issue 9, pp. 1189-1201. (Abstract).

Redmon, J. et al., "YOLO9000: Better, Faster, Stronger", arXiv:1612.08242, 2016, 9 pages.

Raynaud, C. et al. "Multi-organ detection in 3D fetal ultrasound with machine learning." Fetal, Infant and Ophthalmic Medical Image Analysis. Springer, Cham, 2017, pp. 62-72.

* cited by examiner

ULTRASOUND PROCESSING UNIT AND METHOD, AND IMAGING SYSTEM

RELATED APPLICATIONS

This application is the U.S. National Phase application under 35 U.S.C. § 371 of International Application No. PCT/EP2019/058865, filed on Apr. 9, 2019, which claims the benefit and priority of Provisional Application Ser. No. 62/658,942, filed Apr. 17, 2018, and of European Application No. 18172400.6, filed May 15, 2018. These applications are hereby incorporated by reference herein, for all purposes.

FIELD OF THE INVENTION

This invention relates to an ultrasound processing unit, in particular for checking alignment of an imaged feature within the field of view.

BACKGROUND OF THE INVENTION

In many applications of ultrasound imaging, in particular for long-term cardiac monitoring, maintaining consistency of probe positioning relative to an imaged anatomical body or region is important. Long term monitoring involves fixing an ultrasound probe in a set position relative to a subject, having a particular region or object of interest within the field of view (FOV), and acquiring ultrasound data using the probe over an extended period of hours or days. This allows for long term monitoring of certain physiological parameters including for instance hemodynamic parameters such as end diastolic or end-systolic ventricular volume, cardiac volume, left-ventricular ejection fraction, stroke volume, cardiac output.

Long-term cardiac monitoring may make use of a transesophageal echocardiography (TEE) probe. However, external chest mounted probes can also be used. Model based segmentation may be used for monitoring the physiological parameters.

Reliable long-term monitoring relies on stability of the probe location, and consistency of the imaged region or object in the field of view. If there is movement of the imaged region within the field of view, accuracy of derived physiological parameters may be reduced. Moreover, if the region of interest, e.g. the left or right ventricle, moves completely outside of the field of view, or moves too close to boundaries of the field of view, it becomes impossible to acquire readings of parameters related the object.

Although the field of view is set accurately at the start of monitoring, over time the probe can become displaced. This results in drifting of the field of view away from the initially centered heart region, which diminishes image quality and accuracy of monitoring results, and so necessitates re-adjustment of the probe.

This poses a problem for long-term monitoring. The FOV must be frequently checked by an operator, to prevent it from drifting by too great an extent (e.g. before to a point at which monitoring becomes impossible). This is tedious for the operator, and also wastes valuable clinical time.

One possible solution would be to configure the ultrasound monitoring system to detect when monitoring of a given parameter becomes impossible due to movement of the monitored region outside the field of view and to instigate an alarm to automatically alert the operator.

This avoids the need for the operator to manually check for drifting of the probe position. However, this has the deficiency that once the alarm sounds, action must be taken immediately, since monitoring has already ceased. This interrupts operators suddenly from previous tasks, causing disruption, and also leads to problematic gaps in monitoring data while the probe is readjusted.

There is a need for an improved means for overcoming the above deficiencies in current long-term ultrasound monitoring.

SUMMARY OF THE INVENTION

The invention is defined by the claims.

According to an aspect of the invention, there is provided an ultrasound processing unit comprising:

a controller, adapted to:

receive ultrasound data representative of an anatomical region and representative of a series of time points, process the data to identify a particular anatomical feature within the data;

perform an alignment check procedure, the procedure comprising determining whether an alignment of the anatomical feature within a field of view of the ultrasound transducer unit is changing over time, and responsive to determining that the alignment is changing, generate an output signal for communicating said determination to a user, and wherein the controller is adapted to determine an estimated time duration until the alignment of the anatomical feature will move outside of a set of one or more defined limits and to generate an information output representative of said time duration.

The invention is based on monitoring for movement of an imaged anatomical feature of interest over time within the field of view, and using this detected movement as a means of alerting operators at an early stage to the likely drifting of the transducer unit field of view. This allows them to make provision for adjusting the transducer unit position at a time which is both convenient and which is before the monitored region moves completely out of view.

Using detected changes in alignment of the anatomical feature has the advantage of permitting early detection of drift of the ultrasound probe acquiring the ultrasound data, and according to some embodiments of permitting estimation as to a likely remaining time before the anatomical feature will move outside of the field of view boundaries.

The processor may be adapted to receive the ultrasound data from an ultrasound transducer unit. This may be an external ultrasound transducer unit. The controller may be operatively coupleable with an ultrasound transducer unit for receiving the ultrasound data. The processing unit may have an interface means, for instance a coupling interface, for instance an interface port, for operatively coupling with an ultrasound transducer unit adapted for acquiring ultrasound data of the anatomical region of interest. The transducer unit may include an ultrasound probe. The ultrasound data may be received in real-time with the data acquisition by the ultrasound transducer unit.

Alternatively, the controller may be adapted to receive or retrieve or access ultrasound data from a data store or memory, either local or remote to the processing unit. In this way, ultrasound data collected at an earlier time may be later processed by the processing unit.

The alignment of the anatomical feature within the field of view may mean a position or location of the anatomical feature within the field of view. This may mean a position of for instance a central point of the feature within the field of view.

The anatomical feature under consideration may be defined in advance, for instance by the controller, or set by a user input. In examples, the anatomical feature may be an anatomical region or a particular anatomical structure or element. Examples include a ventricle of the heart (left ventricle or right ventricle), an atrium of the heart, a valve of the heart, the myocardium, the endocardium.

One anatomical feature may be identified, or more than one anatomical feature may be identified in examples. The alignment check procedure may be based on detecting change in alignment of more than one anatomical feature.

Image segmentation may in some examples be used to identify the anatomical feature.

The controller is adapted to receive or access or retrieve ultrasound data. Ultrasound data may in some examples be ultrasound image data. It may be Doppler ultrasound data. It may be both.

Identifying the anatomical feature may comprise identifying the anatomical feature within one or more image(s) or image frame(s) represented by the data. Identifying the anatomical feature may include identifying a location or position of the anatomical feature within the field of view.

According to advantageous embodiments, the received ultrasound data is representative of at least a region of the heart. Embodiments of the invention find particularly advantageous application for use in long-term monitoring of the heart. The processing unit may hence be for long-term cardiac monitoring.

The alignment check procedure may comprise determining an alignment parameter representative of an alignment of the anatomical element within the field of view and determining whether a value of this parameter is changing over time. As noted above, this parameter may be a position of the anatomical feature within the field of view. The parameter may be a distance to a boundary or border of the field of view in examples.

The output signal may by way of example be an information output for communication to an external computer or terminal such as a patient monitor. The patient monitor may then generate a sensory output. The output signal may itself be or comprise a sensory output such as an auditory output.

The controller may be adapted to generate the output signal both in the case that changes in the alignment of the anatomical feature are detected and in the case that changes are not detected. In this way, an operator is provided with maximum information.

In examples, the alignment may correspond to a distance of the anatomical feature from a boundary of the field of view.

In examples, the estimated time duration may be an estimated time duration until the alignment of the anatomical feature will move outside of a field of view of the ultrasound transducer unit.

According to advantageous embodiments, the alignment check procedure may further comprise performing an initial check procedure comprising determining whether an initial alignment of the anatomical feature within the field of view is within one or more defined limits, and responsive to determining the alignment is outside of said defined limits, generating an output signal for communicating said determination to a user.

The initial check procedure is performed in advance of determining whether there is movement in the alignment. This allows any starting misalignment of the anatomical feature within the field of view to be detected, and the operator alerted by means of the output signal. Subsequently, responsive to determining that the alignment is within said defined limits, the controller may continue monitoring for any changes in said alignment over time.

By way of example, the initial alignment check procedure may for example comprise determining an alignment parameter representative of an alignment of the anatomical element within the field of view and determining whether a value of this parameter is within one or more defined thresholds.

According to particular examples, the initial alignment check procedure may comprise identifying a location of the anatomical feature within the field of view and determining based on said identification whether the feature lies within one or more defined boundaries within the field of view. The boundaries may for instance be inset from the extreme peripheral edges of the field of view, so as to define an inner sub-region, and a set of one or more outer margins. The controller may determine whether the anatomical feature is within the inner sub-region. In some cases, positioning of the anatomical feature within outer margins of the field of view may diminish quality of measured parameters and/or image quality.

The alignment check procedure comprises determining whether an alignment of the anatomical feature within a field of view of the ultrasound transducer unit is changing over time.

The alignment check procedure may comprise determining whether the alignment is changing in an on-going manner.

On-going means a change in the alignment which continues in changing over multiple time points, e.g. over multiple ultrasound frames. Ongoing may be characterized as a change in the alignment which continues to change for at least a minimum defined time threshold.

It may be characterized as a change in a position of the anatomical feature within the field of view relative to an initial position which continues over multiple time points, for instance which continues for at least a minimum time threshold. For example, it may be characterized as an increase in distance from an initial position of the anatomical feature which continues to increase for at least a minimum time threshold.

In examples, the alignment check procedure may comprise determining whether there is a change in alignment which continues in changing for a minimum threshold time. This may mean determining whether there is a change in alignment which continues to increase for a minimum threshold time, i.e. that the change in alignment (relative to a notional defined start point) continues to grow or expand for at least a minimum threshold time.

The alignment check procedure may additionally or alternatively comprise identifying changes in the alignment exceeding a minimum threshold size. The alignment check procedure may take only such changes into account when determining whether the alignment is changing. This may comprise identifying change in the position of the anatomical feature within the field of view of a minimum threshold size, and/or movement or shift of the feature within the field of view of a minimum threshold distance from an initial position.

The alignment check procedure may comprise determining whether the alignment is continually changing over time, e.g. continuously changing. Or it may comprise determining whether there have occurred multiple discrete changes at plural time points.

A change in alignment or movement or shift exceeding a certain threshold may provide an indirect indication that alignment is close to moving (or even has moved) outside of acceptable limits, enabling this drift to be arrested before monitoring becomes impossible.

The alignment check procedure may in some examples comprise:

determining whether there is any net change in the alignment over a defined time period; and/or determining whether there is any net change in the alignment over a single heart cycle or portion of a heart cycle.

Each of these examples aims to exclude temporary or transient movements, for instance periodic cyclical movements, such as the contraction and expansion of heart ventricles. By looking for net change over a heart cycle for instance, the cyclical motion of the heart itself may be distinguished from slower and more persistent drift of the anatomical feature (of in this case the heart) within the field of view. Looking for a net change over a certain time period similarly excludes short-term local fluctuations in position of anatomical features, or in the position of the ultrasound transducer unit relative to the body.

A single heart cycle may be defined for instance as from any point during the heart cycle back to that same point in the heart cycle. To exclude beating, the heart cycle may be defined for example as from a point in mid-diastolic phase (i.e. during the middle of diastole) back to mid-diastolic phase.

The alignment check procedure may in some examples comprise identifying changes in the alignment which persist for a minimum threshold time. By persist may be meant changes which do not reverse or disappear for at least that minimum threshold time. Hence the alignment check procedure may comprise identifying changes in said alignment which, for a minimum threshold time, do not reverse. The alignment check procedure may take only such changes into account in determining whether the alignment is changing.

This aims at excluding changes in alignment which are merely transitory or temporary, thus capturing true long-term drift of the anatomical feature within the field of view.

According to an advantageous set of embodiments, the alignment check procedure comprises deriving, based on any detected changes in alignment, a corresponding speed of movement of the anatomical feature within the field of view represented by the changes.

Here a speed or rate of change of alignment is determined.

Speed of movement may for example be defined in terms of relative units, relative to the field of view for instance. It may be based on a self-defined or custom co-ordinate system in examples.

Deriving a speed of movement of the anatomical feature enables highly useful technical information to be derived concerning the nature of the detected alignment shift. This may allow genuine long term drift to be distinguished from short-term transitory shifts or jumps. For example, very fast abrupt changes might be discounted from determination of change in the alignment, as they are likely to be caused by local and short term factors. Slower changes may however be taken into account as more representative of long term drift.

Accordingly, the alignment check procedure may comprise detecting changes in the alignment corresponding to a speed of movement falling below within a defined range of speed values. The alignment check procedure may in some examples take only such changes into account in determining whether an alignment of the anatomical feature is changing over time. In particular examples for instance, the alignment check procedure may comprise detecting changes in the alignment corresponding to a speed of movement falling below a defined maximum threshold speed. As noted, this allows sudden, abrupt changes to be discounted. Slower changes may be more representative of long-term drift.

Frequency of changes may also be detected. The alignment check procedure may comprise identifying changes which exceed a given defined speed threshold and a given defined frequency threshold. Such changes may be indicative of for instance coughing, which action can lead to sudden or rapid displacement of the ultrasound probe collecting the data. Detecting such changes permits this outcome to be avoided by alerting users/clinicians early.

Determining a speed of movement also facilitates other advantages.

According to one or more examples, the controller may adapted to determine, the estimated time duration until the alignment of the anatomical feature will move outside of the set of one or more defined limits based on said determined speed of movement.

Hence, advance warning can be derived of a future movement of the anatomical feature outside of acceptable limits. The one or more defined limits may in examples be understood as outlined above in relation to the initial check procedure. For example, they may correspond to one or more defined boundaries within the field of view, for example boundary lines. Boundaries may mean for instance defined minimum distances from the outer edges of the field of view. They may alternatively correspond to one or more defined limits of a particular alignment parameter.

Preferably the controller is further adapted to generate an information output representative of the derived time. This may be communicated to a user output for communication to an operator. This enables an operator to plan for making adjustment of the probe to prevent drift of the anatomical feature outside of the field of view, before such drift in fact happens.

In accordance with one or more embodiments, the controller may be adapted to apply an image segmentation procedure or landmark detection procedure to the ultrasound data. Identifying the anatomical feature may then be performed based on the image segmentation or landmark detection procedure.

Image segmentation permits anatomical context to be derived or applied to ultrasound images or image data or data. This permits a location of the anatomical feature to be identified, and thus permits an alignment of the feature to be derived, and changes in the alignment to be detected. The image segmentation procedure is preferably a model-based image segmentation procedure.

A landmark detection procedure is an image processing procedure which is based on identifying coordinates or boundary lines of a specific landmark, and using this to provide anatomical context to image data.

For either procedure (segmentation or landmark detection), the algorithms forming the procedure may comprise or employ machine-learning or deep-learning techniques. These are terms of the art and refer to procedures which use statistical techniques to provide systems with an ability to learn (i.e. to progressively improve performance on a given task) based for instance on feedback or past results.

Generating the output signal may comprise generating a sensory output for alerting an operator, e.g. an auditory signal, such as an alarm.

The ultrasound processing unit may in certain embodiments be for determining and monitoring a hemodynamic parameter. The unit may be a cardiac ultrasound monitoring unit. The unit may be a hemodynamic parameter ultrasound monitoring unit.

According to advantageous embodiments, the controller may be further adapted to process the acquired ultrasound data so as to derive one or more hemodynamic parameters of the heart. The controller may be further adapted to process the acquired ultrasound data so as to monitor one or more hemodynamic parameters of the heart over time.

Hemodynamic parameters may include for example one or more of: end diastolic or end-systolic ventricular volume, cardiac volume, left-ventricular ejection fraction, stroke volume, and cardiac output.

Examples in accordance with a further aspect of the invention provide an ultrasound imaging system comprising:

an ultrasound transducer unit for acquiring ultrasound data representative of an anatomical region of interest; and an ultrasound processing unit according to any of the embodiments or examples outlined or described above or below, and adapted to receive said ultrasound data from the ultrasound transducer unit.

The ultrasound transducer unit may comprise an ultrasound probe. The transducer unit may comprise one or more ultrasound transducers for acquiring ultrasound data. The transducer unit may comprise in some example an ultrasound array transducer.

The ultrasound imaging system may in examples be for monitoring a hemodynamic parameter. The system may be a cardiac ultrasound monitoring system. The system may be a hemodynamic parameter ultrasound monitoring system.

Examples in accordance with a further aspect of the invention provide a patient monitoring device comprising:

a patient monitoring unit; and an ultrasound processing unit in accordance with any of the examples or embodiments outlined or described above or described below, or an ultrasound imaging system in accordance with any example or embodiment described above or below.

The patient monitoring unit may be operatively coupled with the ultrasound processing unit or ultrasound imaging system. In examples, the ultrasound processing unit is adapted to determine or monitor a physiological parameter, e.g. a hemodynamic parameter. The patient monitoring unit may be adapted to receive data representative of the said determined values for storage or analysis or display for instance.

Examples according to a further aspect of the invention provide an ultrasound processing method, comprising:

receiving ultrasound data representative of an anatomical region of interest;

processing the data to identify a particular anatomical feature within the data;

performing an alignment check procedure, the procedure comprising determining whether an alignment of the anatomical feature within a field of view of the ultrasound transducer unit is changing over time; and responsive to determining that the alignment is changing, generating an output signal for communicating said determination to a user.

The method may be performed by a processor or controller. The method may be a computer-implemented method.

According to one or more embodiments, the alignment check procedure may comprise deriving, based on any detected changes in the alignment, a corresponding speed of movement of the anatomical feature within the field of view represented by the changes.

The method may further comprise determining, based on said determined speed of movement, an estimated time duration until the alignment of the anatomical feature will move outside of a set of one or more defined limits, and preferably wherein the controller is further adapted to generate an information output representative of said time.

BRIEF DESCRIPTION OF THE DRAWINGS

Examples of the invention will now be described in detail with reference to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound processing unit. A controller of the unit is adapted to receive ultrasound data of an anatomical region, for example of the heart, over a series of time points. The controller processes the ultrasound data over a period of time to monitor and detect whether alignment of a particular anatomical feature represented in the data relative to a field of view of the transducer unit is changing over time. In the event that the alignment is changing, the controller generates an output signal for communicating this to a user, allowing a user to be alerted at an early stage to likelihood of misalignment and loss of imaging or measurement capability.

The processing unit may be for processing ultrasound data to monitor one or more cardiac physiological parameters, for instance hemodynamic parameters. The invention finds advantageous application in particular for long term ultrasound monitoring, in particular long-term cardiac monitoring.

The alignment may be characterized or quantified in different ways, using different parameters for instance.

Figure 1:
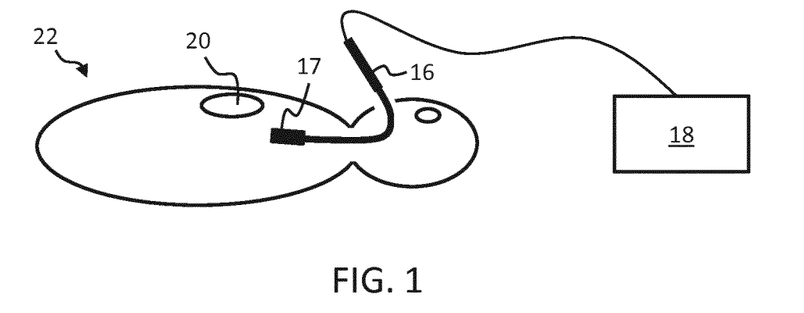
FIG. 1 schematically depicts an example ultrasound processing unit in accordance with an embodiment.

FIG. 1 schematically depicts an example ultrasound processing unit according to invention, as coupled with an ultrasound transducer unit 16 for acquiring ultrasound data. The ultrasound processing unit comprises a controller 18.

The transducer unit and processing unit may be provided together according to one aspect of the invention, to form an ultrasound imaging system according to the invention. Alternatively, the ultrasound processing unit (comprising controller 18) may be provided alone according to a further aspect of the invention, the processing unit being adapted to receive ultrasound data from an external source. This external source may be an ultrasound transducer unit, or may be a different source, for instance a data store.

In the descriptions which follows, options and variations described in relation to an ultrasound imaging system should be understood as applicable equally to an ultrasound processing unit according to the invention (and vice versa).

FIG. 1 shows the basic hardware configuration in accordance with one example of the processing unit or imaging system of the invention. The arrangement comprises an ultrasound transducer unit 16, in this case in the form of a transesophageal echocardiography (TEE) probe. The probe comprises at an imaging end an ultrasound transducer array 17. Optionally, the transducer array is operable to generate ultrasound beams having controllable directionality, but this is not essential to the invention.

In use, the probe is positioned by a clinician in a suitable positon such that an anatomical feature of interest within the heart 20 of a subject 22 is within a field of view of the transducer array 17 of the transducer unit 16. In this case, as the transducer unit is a TEE probe, the TEE probe is located in a suitable position within the esophagus of the subject 22.

The probe is operatively coupled to a controller 18 of the ultrasound processing unit which according to one or more embodiments controls acquisition of ultrasound image data using the transducer unit 16 representative of the heart. The controller and probe together may form an ultrasound imaging system in accordance with one or more embodiments of the invention.

By way of illustration, steps implemented by the controller 18 will now be described by way of reference to an example in which the anatomical feature of interest is the left ventricle of the heart. However, it is to be understood that the same procedural steps may be applied equally to any other anatomical feature, either of the heart, or of any other region, structure or element of the body.

The controller 18 is configured to receive ultrasound data from the ultrasound transducer unit 16. The controller may be configured to control the transducer unit in acquiring the data, or the transducer unit may be controlled by a separate dedicated command unit or processor for instance. These options will be explained in greater detail below.

The transducer unit 16 acquires ultrasound data continuously or recurrently on an on-going or continuing basis, so as to acquire ultrasound data representative of a series or continuum of time points. Preferably, this covers multiple cardiac cycles.

In this way data is acquired over an extended period of time, covering multiple time points. Data may be received continuously, or ultrasound data may be received periodically, at regular intervals. Intervals may for instance be every minute, or every 5 minutes, or every 15 minutes, or any other desired interval, depending upon desired density of data. Data from the transducer unit 16 may be sampled periodically at such regular intervals for instance.

The acquired ultrasound data may be ultrasound image data. The data may be processed in order to derive one or more ultrasound images. Multiple image frames may be generated from ultrasound data acquired over multiple time points, each frame representative of a different time point. Changes in alignment of an anatomical feature may then be derived by identifying changes in the alignment between frames.

Preferably, 3D ultrasound image data is acquired, permitting more accurate, or at least more straightforward, tracking of alignment of an anatomical feature of interest within the body, relative to a field of view. However, 2D image data may also be used. Approaches to using 2D data in determining alignment of the anatomical feature will be described in greater detail in passages to follow.

The controller 18 is further configured to process received ultrasound data to identify an anatomical feature of interest represented in the data, within the field of view of the ultrasound transducer unit. For the purposes of the present example, the anatomical feature will, by way of example, be taken to be the left ventricle of the heart.

Processing of the data may comprise performing an image segmentation procedure on the data, e.g. on ultrasound images derived from the data.

Image segmentation is a well-known procedure in the field of image processing whereby a (digital) image is partitioned or divided into a plurality of sectors or regions according for instance to common properties possessed by pixels falling within those regions. For instance, image segmentation may typically be applied to identify or locate objects within a broader image and to identify boundaries within images (e.g. lines, curves, contours).

In the present application, image segmentation may allow an ultrasound image represented by the ultrasound data to be processed to identify or locate anatomical bodies or regions within the image and locate boundaries of said bodies or regions.

The image segmentation may preferably be model-based image segmentation. Model based segmentation makes use of common structural or geometrical patterns characteristic of a particular anatomical region or body to more accurately identify anatomical bodies within captured images. In particular, a probabilistic model is typically employed concerning likely shapes or contours for certain anatomical features. The parameters encoded within this model may then be applied as constraints when segmenting image data to more accurately and precisely identify boundaries of particular geometrical features or regions which are of interest.

For instance, for the purposes of advantageous examples of the present invention, model-based segmentations may make use of a model associated with the cardiac region, or may more particularly make use of a model of the left or right ventricular region, including the mitral valve, tricuspid valve and left or right ventricular outflow tract. For the purposes of the present example, model-based segmentation may make use of a model associated with the left ventricle.

Suitable model-based segmentation algorithms for this purpose are known in the art. See for example Ecabert et al., "Automatic Model-Based Segmentation of the Heart in CT Images". IEEE TRANSACTIONS ON MEDICAL IMAGING, 27(9), 2008 which describes model-based segmentation approaches which could be applied to ultrasound data acquisitions of the present invention. See also US 2015/0011886 which describes model based segmentation procedures as may be applied in embodiments of the present invention.

Figure 2:
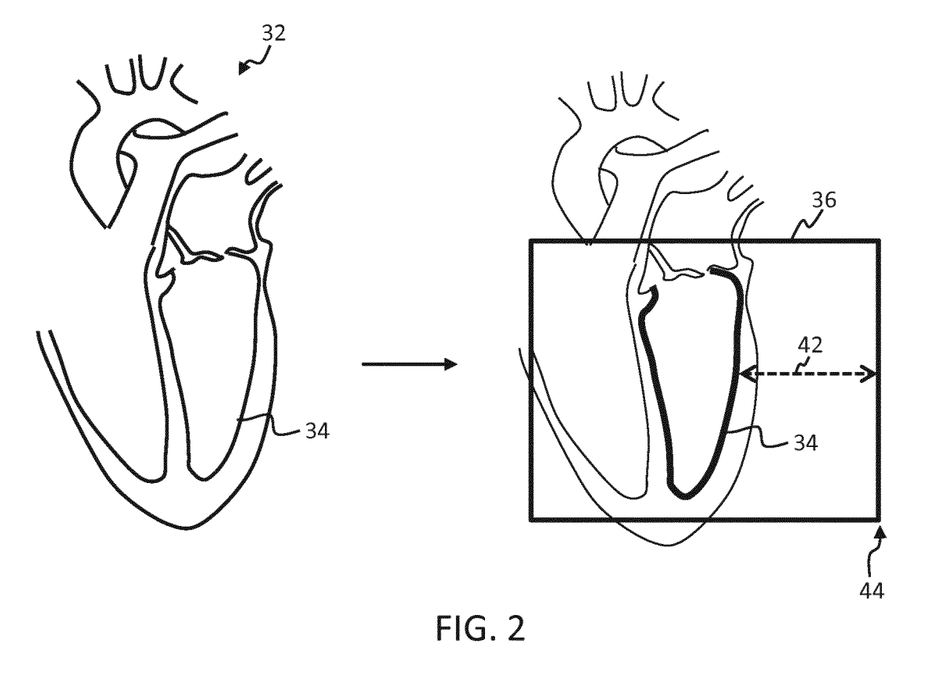
FIG. 2 illustrates alignment of an anatomical feature within a field of view of a transducer unit.

For the purposes of the present example, identification of a left ventricle within acquired ultrasound data is illustrated in FIG. 2. The ultrasound transducer unit 16 is positioned as shown in FIG. 1 so that a field of view of the unit is directed toward the heart 32. The right-hand side of FIG. 2 schematically depicts the field of view 36 of the transducer unit, which for the purposes of this example is shown as roughly centered around the left ventricle 34 (i.e. the anatomical feature of interest in this example).

It is emphasized that although the field of view is depicted in FIG. 2 as rectangular, this is purely schematic. In practice, the field of view may typically have a conical or frusto-conical shape (i.e. a conical frustum). The field of view may be three dimensional or two-dimensional, e.g. a slice through a cone or conical frustum. The field of view may in further examples take any other shape.

In addition to identifying the anatomical feature, the controller 18 is also preferably adapted to process the data to derive a physiological parameter, e.g. a hemodynamic parameter. By processing the data over multiple time points to derive the parameter, the parameter may be monitored over time. The controller generates an information output representative of the derived parameter value(s). This may be communicated in examples to e.g. to a patient monitoring device. This unit may be external to the ultrasound imaging system or processing unit of the invention, or the ultrasound imaging system or processing unit may be incorporated as part of a patient monitoring device (i.e. be comprised by the patient monitoring device).

Example hemodynamic parameters include, by way of non-limiting and non-exclusive example, end-diastolic or end-systolic ventricular volume, cardiac volume, left-ventricular ejection fraction, stroke volume, and cardiac output.

Deriving the physiological parameter may also make use of an image segmentation procedure. By way of example, where the physiological parameter is for instance end-diastolic left ventricular volume, image segmentation may be applied to derive ultrasound images, permitting an outline of the left ventricle at end diastole to be derived, e.g. as shown in FIG. 2. This can then be used to determine a volume of the left ventricle at this point, permitting the parameter to be thus derived.

More particularly, the controller 18 may make use of model-based segmentation to provide anatomical context to the image. Model based segmentation permits locating of different anatomical features or elements of for instance the heart, and in particular the cardiac chambers. Based upon this, the controller may derive one or more physiological parameters.

A single image segmentation procedure is preferably performed on acquired ultrasound data and this used both to identify the anatomical feature of interest within the acquired data and to derive and monitor over multiple time points one or more physiological parameters.

Once the anatomical feature of interest has been identified in the data, in this case the left ventricle, for example by image segmentation, the controller 18 performs an alignment check procedure. This will now be described with reference to FIGS. 2 and 3.

Figure 3:
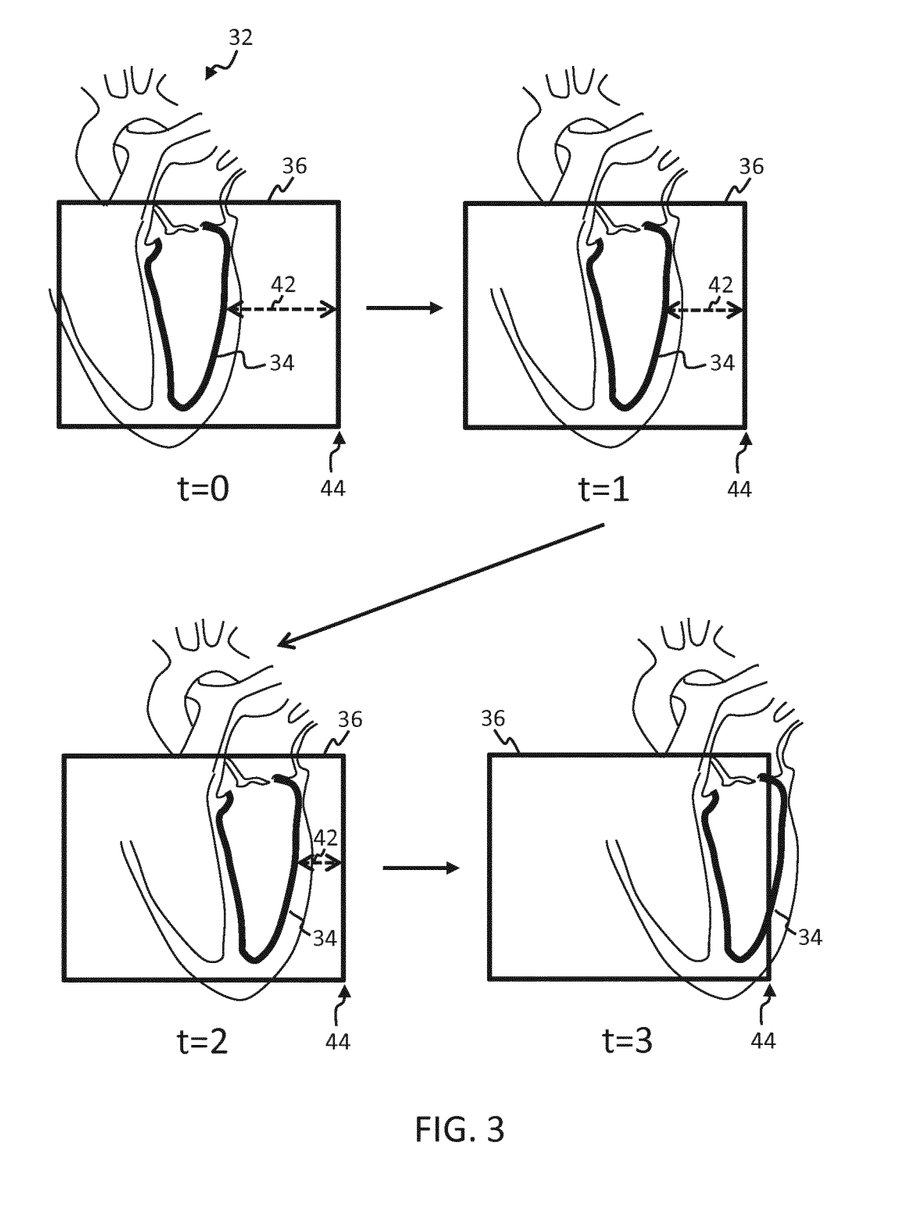
FIG. 3 illustrates drift of alignment of the anatomical feature over time.

FIG. 3 schematically depicts four ultrasound image frames derived from ultrasound data acquired over a set of four time points, t=0, t=1, t=2, and t=3. Each frame is shown schematically in terms of a corresponding field of view 36 of the ultrasound transducer unit, with its alignment relative to the heart 32 depicted. The alignment of the left ventricle 34 within the field of view 36 at each time point is represented in terms of a distance 42 or displacement between a left-hand wall of the left ventricle (anatomically left, but shown on the right within the context of FIG. 2) and a right-most boundary 44 of the field of view.

The four frames illustrate drifting of the left ventricle within the field of view, with the alignment 42 of the left ventricle within the field of view changing over time. At time t=0, the left ventricle 34 is roughly centered in the field of view 36. At time t=1, the left ventricle has begun to drift toward the right in the field of view, with the distance 42 to the right hand wall reducing. At t=2, the left ventricle is very close to the right-hand wall. By t=3, the left ventricle is no longer completely contained within the field of view, meaning that the related physiological parameter (such as end-systole or end-diastole volume) can no longer be derived, so monitoring of this parameter is no longer possible, or at least that monitoring capability is substantially reduced, e.g. has reduced accuracy.

The controller 18 is adapted to monitor the alignment of the left ventricle, via the characterizing parameter of the distance 42 to the field of view boundary and to determine whether the alignment of the left ventricle is changing over time.

In the example case of FIG. 3, the alignment is changing. The controller 18 hence identifies this, and responsive to determining that the alignment is changing, the controller generates an output signal for communicating the determination to a user. This may then generated an output signal for alerting the user to the drifting of the left ventricle 34 within the field of view 36, permitting the ultrasound transducer unit 16 to be repositioned, before the left ventricle drifts outside of the field of view altogether, as at time t=3 of FIG. 3.

The controller 18 may generate such an output signal whether or not the alignment is detected as changing, so as to provide the user with maximal information.

In the case that the system or transducer unit 16 is configured to acquire 3D ultrasound image data, monitoring or tracking of the anatomical feature alignment or position may be performed straightforwardly, based on the results of identifying the anatomical feature in the image. This identification provides a 3D positioning of the feature within the field of view, permitting changes in this positioning relative to the field of view between frames to be identified.

The system or transducer unit 16 may also be configured to acquire 2D ultrasound image data, which permits use of a lower cost probe. In this case, a possible approach to tracking alignment is to separate in-plane drift of the anatomical feature (i.e. as depicted in FIG. 3, wherein the left ventricle moves between the boundaries of a single-plane field of view) and out-of-plane drift (i.e. where the scanning plane has been moved in the normal direction, or rotated, such that the new scanning plane lies adjacent to the original scanning plane).

For the in-plane-drift, a similar approach as in the 3D data case can be used based for instance on a segmentation of the 2D image. For the detecting out-of-plane drift, possible approaches may include to detect sudden appearance of previously absent anatomical structures in the image. This may, for example, be performed using landmark detectors, for instance based on deep learning algorithms.

In particular examples, the processing unit or ultrasound imaging system may be configured to communicate, in combination with the signal output, instructions for guiding the operator in adjusting the probe to achieve an optimal field of view alignment, (e.g. using arrows or a visualization of the probe controls). This may be output via an associated user output display, which may be part of an imaging system in examples or may be external to the system in other examples.

Different options exist for optimizing the alignment check procedure.

According to certain examples, the controller 18 may generate the output signal for altering the operator as soon as a change in the alignment of the anatomical feature (e.g. the left ventricle 34) changes. This gives maximal warning time. For instance, in the example of FIG. 3, the controller may generate an output signal as soon as drift is detected at t=1.

However, this approach is liable to false positives, since there may frequently occur movement of an anatomical feature 34 within the field of view 36 which is only temporary or transient, and which is not indicative of genuine long-term drift in alignment. For instance, in the context of the heart, it is not desirable that the cyclic pulsating of the heart chambers should trigger an alignment drift warning.

Hence, according to one set of examples, the controller 18 is configured to determine whether alignment is changing in an on-going or consistent manner. This may comprise determining whether alignment is continuing to change in a common direction for at least a minimum period of time. This would then exclude very short-term temporary alignment changes. For instance, in the schematic example of FIG. 3, the controller may be configured to wait until a time t=2 before concluding that the change in alignment is continuing in an on-going manner.

Of course, the example of FIG. 3 is highly schematic, and drift in alignment typically occurs over minutes, rather than seconds, meaning that a minimum drift period may be defined, and the controller 18 configured to determine whether there is change in the alignment on-going in a consistent direction for at least said minimum drift period.

According to further examples, the controller 18 may be adapted to determine whether a change in alignment exceeds a minimum threshold size. The size here may refer to any parameter which is used to characterize or quantify the alignment. In the present example, the size refers to the distance 42 or displacement to the field of view 36 right-hand boundary 44. Hence in this example, the controller may only conclude that there is true drift in alignment in the case that a detected change in this distance 42 exceeds a certain threshold size. The threshold may be set in advance and stored by the controller for example, or may be user-definable in examples, for instance by means of a user input device communicable with the controller.

According to one or more examples, the controller 18 may monitor change in the alignment over a particular minimum time period or over a single or multiple heart cycles, and determine whether there is any net change in alignment over these periods. If there is no net change, the controller may discount any intermediate changes detected during these periods. This again aims at excluding false positive detection of drift.

According to one or more examples, the controller 18 may be adapted to identify or detect changes in alignment which correspond to movement of the anatomical feature within the field of view to within a threshold distance or range of a defined boundary of that field of view. In certain examples, only these changes in alignment may be taken into account. For example, the controller may be adapted to detect when the field of view has shifted so that the feature of interest is within 5 mm of a boundary of the field of view, or 10 mm, or 2 mm or any other distance. The distance may for example be in pixel units or true units or other any other units, including arbitrary units. The boundary may be an extreme edge or border of the field of view or may be a margin boundary inset from the extreme edge.

In one or more examples, said threshold distance from the boundary may be varied or set based on a patient's condition. For instance, for very sick patients, the threshold distance from the boundary to be reached before an alert is triggered may be increased (i.e. further from the boundary), so that clinicians are warned of potential loss of monitoring capability further in advance.

The controller 18 may determine net change in alignment 34 over a complete cardiac cycle or over several cardiac cycles, for instance over several seconds covering one breathing cycle.

The controller 18 may in certain examples be configured to identify changes in the alignment of the anatomical feature which persist for a minimum threshold time. By persist is meant do not reverse; the change in alignment relative to an initial alignment is still present after a minimum threshold time. The controller may be configured to only take into account such persistent alignment changes in determining whether the alignment is changing over time, and thus whether to alert the operator.

According to a particularly advantageous set of embodiments, the alignment check procedure performed by the controller 18 comprises determining a speed or rate of change of alignment of the anatomical feature (e.g. the left ventricle 34) within the field of view 36. This may mean determining a corresponding speed of movement of the anatomical feature within the field of view represented by the changes in alignment. Determining such a speed permits two main capabilities. First, it is possible to estimate a remaining time until the anatomical feature will drift beyond acceptable or observable limits, allowing operators to be warned in advance and given time to plan re-adjustment of the probe. Second, it permits means of categorizing different kinds of alignment changes (different kinds of movement), and discounting alignment changes which are particularly sudden or abrupt. These are less likely to be representative of true long-term drift of the anatomical feature, but rather of short-term transient changes.

In one set of examples, a rate of change of the alignment (speed of movement) is determined and changes in the alignment corresponding to a speed of movement falling below a defined maximum threshold detected. In this case, the controller 18 looks for changes in alignment which are relatively slow. In examples, the controller may take only such changes into account, with more abrupt or rapid changes more likely to be indicative of short term transient shifts.

In other examples, the controller 18 is adapted to identify alignment changes which exceed a certain speed threshold, i.e. identify abrupt changes, and monitor for any recurrent frequency of such changes over multiple time points. For example, sufficiently abrupt changes in the heart or left ventricle alignment, occurring with a particular regular frequency, may be due to frequent coughing. If frequent coughing is thus detected, the controller may generate a corresponding information output for alerting or informing an operator that the position of the ultrasound transducer unit may become unstable.

According to advantageous embodiments, the alignment is tracked over time to determine a speed of movement of the anatomical feature, as described above, and this speed used, in combination with a known present alignment or position of the feature, to determine an estimated time at which the feature will move outside of the acceptable alignment limits. For example, in the schematic example of FIG. 3, based on a determined speed at time t=1 of the left ventricle 34 toward the right wall 44, the controller 18 could estimate that the left ventricle will move beyond the right wall boundary 44 at time t=3 (or just before), and this information could be provided to the operator to warn them.

Of course, in practice, typically a warning of minutes rather than seconds can be given, allowing the operator time to plan re-adjustment of the transducer unit 16.

By way of a simple example, the alignment might be tracked recurrently over an extended period of time (e.g. over ultrasound images acquired every minute or every 15 minutes for instance). If it is detected by the controller 18, for example, that the distance 42 to the field of view 36 border 44 is decreasing with an average rate of 1 mm per 10 minutes, and the current distance to the border is 3 mm, it is inferred that the field of view border will be reached in 30 minutes. At this point, monitoring of an associated physiological parameter will become unreliable or impossible.

An appropriate warning may then be generated for communication to the operator. Hence the operator is warned that cardiac monitoring may become unreliable in 30 minutes.

Where there is sufficient alignment data available (e.g. alignment monitoring over at least several cardiac cycles), more complex approaches to determining the remaining time may be applied, such as for instance a Kalman filter, which permits extrapolation of the remaining time from the collected series of measurements.

In the scenario above, the ultrasound imaging need not take place continuously beat-to-beat for 30 minutes. The imaging may sample the volume periodically to infer the change in position that is occurring.

In examples, the output signal may be configured in different ways. The imaging system or processing unit itself may comprise means for communicating the outcome of the alignment check to the operator, for instance a display, or a speaker. In other examples, the signal is communicated to an external device, which communicates to the operator. The signal may take the form of an alert or alarm.

The output signal may be configured based on patient-specific information. The output may for instance indicate whether the monitored anatomical feature will move outside of the field of view within a particular monitoring period of the patient. For example, if the patient is checked every 60 minutes, output information may indicate whether the monitored anatomical feature will move outside of the field of view within the next 60 minutes.

According to advantageous examples, the controller 18 is configured, as part of the alignment check procedure, to perform an initial check procedure in which an initial alignment of the anatomical feature (e.g. the left ventricle 34) within the field of view 36 is determined. From this it can be determined if there is any initial misalignment. If the alignment of the anatomical feature is initially outside of defined acceptable limits, an information output may be generated to communicate this to an operator so that the alignment of the transducer unit can be adjusted.

The acceptable limits may be defined in advance and for instance stored in the controller 18, or may be user defined. The limits may for instance pertain to maximum or minimum acceptable values of the particular parameter by which the alignment is characterized or quantified. In the example of FIGS. 2 and 3 for instance, the acceptable limits may be defined in terms of a minimum acceptable value of the distance 42 to the field of view 36 boundary. If the anatomical feature (e.g. left ventricle) has an (initial) alignment which corresponds to a distance 42 from the boundary being less than this limit, then the controller generates an information output to inform the operator.

In the above example, a distance 42 to the field of view boundary 44 was used as the parameter by which alignment of the anatomical feature is defined. However, in other examples, any other suitable parameter may be used. Non-limiting examples include a position of the anatomical feature within the field of view (e.g. a co-ordinate position, defined in terms of a local co-ordinate system of the field of view), distance from any of the other boundaries of the field of view, an average distance from a plurality of boundaries, or a proportion of the anatomical feature which is contained within the field of view. Although the distance to the field of view boundary was measured from an (anatomically) leftmost wall of the left ventricle 34, it could be measured from any other point, e.g. a central point such as a centroid of the anatomical feature.

Although in the above example, processing of the ultrasound data to identify the anatomical feature of interest is performed using an image segmentation procedure, use of image segmentation for this purpose is not essential. In other examples, different approaches may be used, including any suitable image processing or analysis algorithm, such as for instance landmark detection.

Landmark detection is an image processing method which is based on identifying coordinates or boundary lines of a specific landmark, and using this to provide anatomical context to image data. An example method for landmark detection in 3D ultrasound data is described in detail for instance in: Raynaud, Caroline, et al. "Multi-organ detection in 3D fetal ultrasound with machine learning." Fetal, Infant and Ophthalmic Medical Image Analysis. Springer, Cham, 2017. 62-72.

An example image processing method for 2D ultrasound data and based on object detection is described in detail in Redmon J and Farhadi A, "YOLO9000: Better, Faster, Stronger", arXiv:1612.08242.

In all cases, algorithms employed in the image processing may make use of or comprise machine-learning or deep-learning techniques. These are terms of the art and refer to procedures which use statistical techniques to provide systems with an ability to learn (i.e. to progressively improve performance on a given task) based for instance on feedback or past results.

An example segmentation procedure making use of machine-learning techniques is described in detail for instance in: Brosch, Tom, et al. "Deep convolutional encoder networks for multiple sclerosis lesion segmentation." *International Conference on Medical Image Computing and Computer-Assisted Intervention*. Springer, Cham, 2015.

According to further examples, image processing methods may be employed capable of detecting drift in the field of view without the need to associate or ascribe anatomical context to different elements of the image, i.e. without the need to identify an anatomical feature as being an anatomical feature. The algorithm may for instance detect shifts or changes in an overall shape or shading pattern forming or constituted by the image. One approach to implementing such methods may for instance include use of recurrent neural networks (RNNs). A recurrent neural network is a class of artificial neural network where connections between units form a directed graph along a sequence. This allows it to exhibit dynamic temporal behavior for a time sequence. This makes such an approach particularly suited to embodiments of the present invention which typically require handing of time-series data.

Although in the above example, the system was illustrated in use for monitoring the heart, the invention is not limited to such application, and in other applications the system may be used in monitoring any other anatomical region, structure or body using ultrasound imaging.

Furthermore, although in the above example, the controller 18 is configured to derive one or more physiological parameters from the ultrasound data, this is not essential, and in other examples, the controller simply performs the alignment check procedure. This may be the case for instance where the ultrasound imaging system or processing unit is simply for collecting ultrasound image data for later analysis. The imaging system may comprise in some examples a memory for storing the acquired ultrasound data.

The system ensures that the collected data has the anatomical feature of interest correctly aligned in the field of view 36.

In the above example, an example ultrasound imaging system was illustrated comprising an ultrasound transducer unit 16 in the form of a transesophageal echocardiography (TEE) probe. The TEE probe may be any suitable form of TEE probe, including for example micro or miniaturized versions that can be inserted orally or nasally. Use of a TEE probe is not essential. In other examples, the ultrasound transducer unit may take the form of a transthoracic echocardiogram (TTE) probe for instance. This probe is placed on the chest or abdomen of the subject in order to get various views of the heart. It provides a non-invasive alternative to a TEE probe.

Reference is made above to generation of an output signal or an information output. This may be for communication to an external device, for instance a patient monitoring device, which may for instance then generate an alert to warn to the operator of the determination by the controller. Alternatively, the controller 18 may comprise a sensory output means, and the output signal may comprise a sensory output for directly alerting the operator.

In any embodiment, there may further be provided a display unit, for instance as part of the ultrasound imaging system. The controller 18 may be adapted to control the display unit to display a visual representation of the output signal or output information.

In certain embodiments, the controller 18 may be communicatively coupled with a patient monitoring device and adapted to communicate the output signal or output information to the patient monitoring device.

In accordance with any embodiment, the ultrasound processing unit, including the controller 18 may be comprised by the ultrasound transducer unit 16.

As discussed above, a first aspect of the invention provides an ultrasound processing unit comprising the controller 18 and adapted to receive ultrasound data and to process the data in order to perform the alignment check procedure and generate the output signal. According to a further aspect of the invention there is provided an ultrasound imaging system comprising an ultrasound processing unit as described above and an ultrasound transducer unit 16 for acquiring the ultrasound data.

Although in the above example, a single integrated controller 18 is provided configured to perform all implemented steps, in further examples, there may be provided a plurality of control units configured to perform different functions within the context of the ultrasound imaging system or ultrasound processing unit.

For instance an ultrasound imaging system may include an imaging unit configured to control the ultrasound transducer unit 16 to acquire ultrasound data at an appropriate sampling rate. As discussed, there may be provided the operatively coupled ultrasound processing unit including controller 18 configured to process the acquired ultrasound data to identify the anatomical feature of interest, i.e. to provide anatomical context to the ultrasound data. The image processing unit may perform model-based segmentation for example. The image processing unit may also process the data to derive the one or more physiological parameters from the data. There may additionally be provided an operatively coupled drift detection unit as part of the ultrasound processing unit, configured to perform the alignment check procedure and to generate the output signal in the event of detected change in the alignment. This may be provided either as part of or external to the controller 18 of the ultrasound processing unit.

Although in the example described above, use is made of an ultrasound probe, in particular a TEE probe or TTE probe, this is not essential to the inventive concept. Any ultrasound transducer unit able to acquire 2D, 3D ultrasound image data and/or also Doppler ultrasound image data (pulsed or continuous wave) of a heart region may be used. This may be an external transducer unit or a semi-invasive probe in accordance with examples.

In examples, embodiments of the present invention are anticipated for use in clinical environments where an ultrasound probe could be placed in a fixed position, such as with transesophageal ultrasound or transthoracic patch probes, for cardiac monitoring e.g. in an intensive care unit, in an operating room, or in an ambulance.

In accordance with one set of embodiments, the ultrasound imaging system or ultrasound processing unit is communicatively coupled with a patient monitoring device and adapted to communicate an output signal or output information representative of the alignment check procedure outcome and/or the movement speed analysis to the patient monitoring device. The patient monitoring device may include a memory for storing received data. The monitoring device may include a display for displaying acquired information to a user (e.g. clinician). The patient monitoring device may be linked with a patient database containing further information about a given patient which could be displayed in conjunction with the derived alignment information.

In accordance with one aspect of the invention, there may be provided a patient monitoring device including a patient monitoring unit and an ultrasound processing unit as described in any example above or below, or as defined in any claim of this application.

There may according to an aspect of the invention be provided a patient monitoring device comprising a patient monitoring unit and an ultrasound imaging system according to any example described above or below or as defined in any claim of this application. The patient monitoring device thus may comprise an ultrasound transducer unit and controller for controlling the transducer unit and determining whether an alignment of an anatomical feature of interest within the transducer unit field of view is changing over time.

The patient monitoring unit may perform the functions associated with the patient monitoring device described above. In particular, the patient monitoring unit may include a memory for storing received ultrasound data. The monitoring device may include a display for displaying acquired information to a user (e.g. clinician). The patient monitoring unit may be linked with a patient database containing further information about a given patient which could be displayed in conjunction with the derived alignment information.

A further aspect of the invention provides an ultrasound processing method. A simple example method is shown in block form in FIG. 4.

Figure 4:
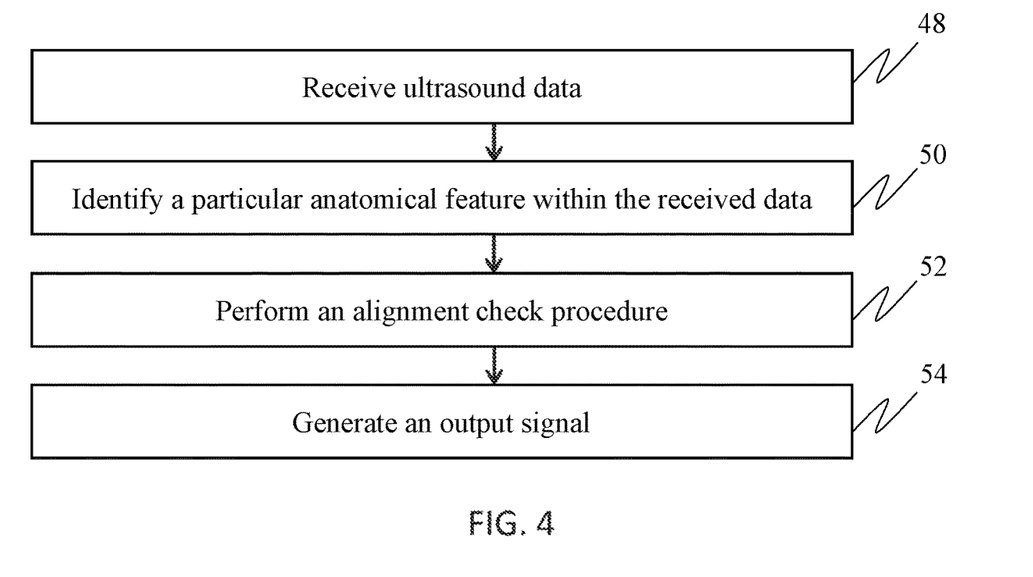
FIG. 4 shows in block diagram form an example ultrasound processing method according to an embodiment.

A first step comprises receiving 48 ultrasound data, for example from an ultrasound transducer unit. Following this, the data is processed 50 to identify a particular anatomical feature within the data (e.g. a left ventricle, as in the example of FIGS. 2 and 3 above). An alignment check procedure 52 is then performed, the procedure comprising determining whether an alignment of the anatomical feature within a field of view of the ultrasound transducer unit is changing over time. Finally, responsive to determining that the alignment is changing an output signal is generated 54 for communicating said determination to a user.

The ultrasound processing method may be performed by a processor or controller. The ultrasound data may therefore be received at a processor or controller. The method may be a computer implemented method.

According to a further aspect, an ultrasound imaging method may be provided, comprising steps of:

acquiring ultrasound data representative of an anatomical region of interest;

processing the data to identify a particular anatomical feature (34) within the data;

performing an alignment check procedure, the procedure comprising determining whether an alignment (42) of the anatomical feature within a field of view (36) of the ultrasound transducer unit is changing over time; and responsive to determining that the alignment is changing, generating an output signal for communicating said determination to a user.

Any option or variation discussed above in relation to the corresponding ultrasound system may be applied equally to any embodiment of the ultrasound processing method. Means for implementing the steps of the method may also be understood from the above discussion in relation to the ultrasound system.

An ultrasound imaging system or ultrasound processing unit according to any embodiment of the present invention may form part of or be provided as part of a wider ultrasound diagnostic imaging system.

Figure 5:
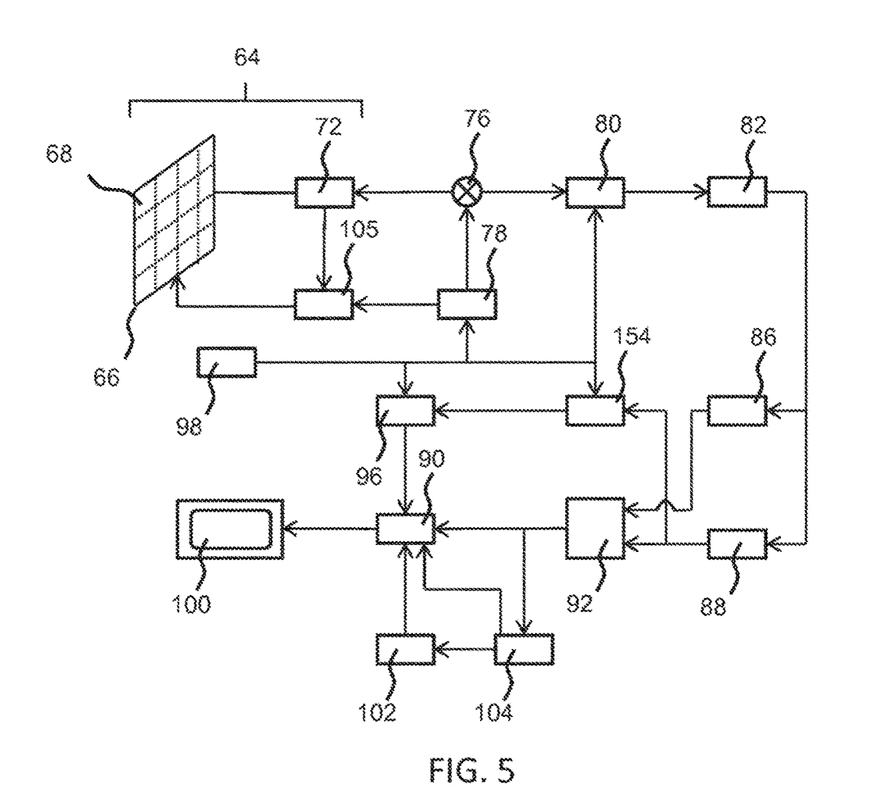
FIG. 5 shows a block diagram of components in an exemplary diagnostic imaging system.

The general operation of an exemplary ultrasound diagnostic imaging system will now be described, with reference to FIG. 5.

The system comprises an array transducer probe 64 which has a transducer array 66 for transmitting ultrasound waves and receiving echo information. Traditionally, piezoelectric materials have been used for ultrasonic transducers. Examples are lead zirconate titanate (PZT) and polyvinylidene difluoride (PVDF) materials, with PZT being particularly popular as the material of choice. Single crystal piezoelectric materials are used to achieve high piezoelectric and electro-mechanical coupling constants for high performance transducers.

Recent developments have led to the prospect that medical ultrasound transducers can be batch manufactured by semiconductor processes. Desirably these processes should be the same ones used to produce the application specific integrated circuits (ASICs) needed by an ultrasound probe such as a CMOS process, particularly for 3D ultrasound. These developments have produced micro machined ultrasonic transducers or MUTs, the preferred form being the capacitive MUT (CMUT). CMUT transducers are tiny diaphragm-like devices with electrodes that convert the sound vibration of a received ultrasound signal into a modulated capacitance.

CMUT transducers in particular are able to function over a broad bandwidth, enable high resolution and high sensitivity imaging, and produce a large pressure output so that a large depth of field of acoustic signals can be received at ultrasonic frequencies.

In this example, the transducer array 66 is a two-dimensional array of transducers 68 capable of scanning either a 2D plane or a three dimensional volume for 3D imaging. In another example, the transducer array may be a 1D array.

The transducer array 66 is coupled to a microbeamformer 72 in the probe which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. The examples described below assume that no analog beamforming is performed by the probe.

The microbeamformer 72 is coupled by the probe cable to a transmit/receive (T/R) switch 76, which switches between transmission and reception modes, and protects the main beamformer 80 from high energy transmit signals in the case where a microbeamformer is not used and the transducer array is operated directly by the main system beamformer. The transmission of ultrasound beams from the transducer array 66 is directed by a transducer controller 78 coupled to the microbeamformer by the T/R switch 76 and a main transmission beamformer (not shown), which receives input from the user's operation of the user interface or control panel 98.

In a typical line-by-line imaging sequence, the beamforming system within the probe may operate as follows. During transmission, the beamformer (which may be the microbeamformer or the main system beamformer depending upon the implementation) activates a sub-aperture of the transducer array. The sub-aperture may be a one dimensional line of transducers or a two dimensional patch of transducers within the larger array. In transmit mode, the focusing and steering of the ultrasound beam generated by a sub-aperture are controlled as described below.

Upon receiving the backscattered echo signals from the subject, the received signals undergo receive beamforming (as described below), in order to align the received signals, and the sub-aperture is then shifted, for example by one transducer element. The shifted sub-aperture is then activated and the process repeated until all of the transducer elements of the transducer array have been activated. For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 78 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations. Further, it is possible to focus a steered beam, wherein the total time delay applied to each transducer element is a sum of both the focusing and steering time delays. In this case, the transducer array is referred to as a phased array.

The transducer controller 78 can be coupled to control a DC bias control 105 for the transducer array. The DC bias control 105 sets DC bias voltage(s) that are applied to the transducer elements.

For each transducer element of the transducer array, analogue ultrasound signals, typically referred to as channel data, enter the system by way of the reception channel. In the reception channel, partially beamformed signals are produced from the channel data by the microbeamformer 72 and are then passed to a main receive beamformer 80 where the partially beamformed signals from individual patches of transducers are combined into a fully beamformed signal, referred to as radio frequency (RF) data. The beamforming performed at each stage may be carried out as described above, or may include additional functions. For example, the main beamformer 80 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 82. The signal processor 82 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 5 only the receiver beamformers 72, 80 are shown, for simplicity. In the complete system, there will also be a transmission chain with a transmission micro beamformer, and a main transmission beamformer.

The function of the micro beamformer 72 is to provide an initial combination of signals in order to decrease the number of analog signal paths. This is typically performed in the analog domain.

The final beamforming is done in the main beamformer 80 and is typically after digitization.

The transmission and reception channels use the same transducer array 66 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 86 and a Doppler processor 88. The B mode processor 86 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 88 processes temporally distinct signals arising from tissue movement and blood flow for the detection of moving substances, such as the flow of blood cells in the image field. The Doppler processor 88 typically includes a wall filter with parameters set to pass or reject echoes returned from selected types of materials in the body.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. In modern mobile ultrasound systems most of the signal processing units described above can be functionally implemented in the ultrasound transducer unit 16.

The structural and motion signals produced by the B mode and Doppler processors are coupled to a scan converter 92 and a multi-planar reformatter 104. The scan converter 92 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 100. In a non-limiting example, the scan converter 92 can also perform a function of the controller 18. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 102 converts the echo signals of a 3D data set into a projected 3D image as viewed from a given reference point as described in U.S. Pat. No. 6,530,885 (Entrekin et al.).

The 2D or 3D images are coupled from the scan converter 92, multi-planar reformatter 104, and volume renderer 102 to an image processor 90 for further enhancement, buffering and temporary storage for display on an image display 100. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 88 and tissue structure information produced by the B mode processor 86 are coupled to a quantification processor 94. The quantification processor produces measures of different flow conditions such as the volume rate of blood flow in addition to structural measurements such as the sizes of organs and gestational age. The quantification processor may receive input from the user control panel 98, such as the point in the anatomy of an image where a measurement is to be made.

Output data from the quantification processor is coupled to a graphics processor 96 for the reproduction of measurement graphics and values with the image on the display 100, and for audio output from the display device 100. The graphics processor 96 can also generate graphic overlays for display with the ultrasound images. These graphic overlays can contain standard identifying information such as patient name, date and time of the image, imaging parameters, and the like. For these purposes the graphics processor receives input from the user interface 98, such as patient name. The user interface is also coupled to the transmit controller 78 to control the generation of ultrasound signals from the transducer array 66 and hence the images produced by the transducer array and the ultrasound system. The transmit control function of the controller 78 is only one of the functions performed. The controller 78 also takes account of the mode of operation (given by the user) and the corresponding required transmitter configuration and band-pass configuration in the receiver analog to digital converter. The controller 78 can be a state machine with fixed states.

The user interface is also coupled to the multi-planar reformatter 104 for selection and control of the planes of multiple multi-planar reformatted (MPR) images which may be used to perform quantified measures in the image field of the MPR images.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound processing unit comprising:
a controller, adapted to:
receive ultrasound data representative of an anatomical region over a period of time, captured by an ultrasound transducer unit;
process the data to identify a particular anatomical feature within the data;
perform an alignment check procedure, the procedure comprising determining whether an alignment of the anatomical feature within a field of view of the ultrasound transducer unit is changing over time, wherein alignment of the anatomical feature within a field of view of the ultrasound transducer unit comprises a determined distance between the anatomical feature and a border of the field of view, and wherein determining whether the alignment of the anatomical feature within the field of view of the ultrasound transducer unit is changing over time comprises determining a change in the determined distance between the anatomical feature and the border of the field of view over time; and
in response to determining that the alignment is changing, generate an output signal for communicating said determination to a user, and
wherein the controller is adapted to determine an estimated time duration until the alignment of the anatomical feature will move outside of a set of one or more defined limits and to generate an information output representative of said time duration, wherein the estimated time duration is an estimated future time duration until the alignment of the anatomical feature will move outside of the field of view of the ultrasound transducer unit.

2. The processing unit as claimed in claim 1, wherein the alignment check procedure further comprises performing an initial check procedure comprising determining whether an initial alignment of the anatomical feature within the field of view is within one or more defined limits, and in response to determining that the alignment is outside of said defined limits, generating an output signal for communicating said determination to a user.

3. The processing unit as claimed in claim 2, wherein the initial alignment check procedure comprises identifying a location of the anatomical feature within the field of view and determining based on said identification whether the feature lies within one or more defined boundaries within the field of view.

4. The processing unit as claimed in claim 1, wherein the alignment check procedure further comprises determining whether there is a change in alignment which continues in changing for more than a predetermined amount of time.

5. The processing unit as claimed in claim 4, wherein the alignment check procedure further comprises determining whether there is a change in alignment which continues in changing in a consistent direction for more than a predetermined amount of time.

6. The processing unit as claimed in claim 1, wherein the alignment check procedure further comprises identifying changes in the alignment exceeding a a predetermined size.

7. The processing unit as claimed in claim 1, wherein the alignment check procedure further comprises:

determining whether there is any net change in the alignment over a defined time period; and/or
determining whether there is any net change in the alignment over a single heart cycle or portion of a heart cycle.

8. The processing unit as claimed in claim 1, wherein the alignment check procedure further comprises identifying changes in said alignment which, for a minimum threshold time, do not reverse.

9. The processing unit as claimed in claim 1, wherein the alignment check procedure further comprises deriving, based on any detected changes in alignment, a corresponding speed of movement of the anatomical feature within the field of view represented by the changes.

10. The processing unit as claimed in claim 9, wherein the alignment check procedure further comprises detecting changes in the alignment corresponding to a speed of movement falling within a defined range of speed values.

11. The processing unit as claimed in claim 9, wherein the controller is adapted to determine said estimated time duration based on said determined speed of movement.

12. The processing unit as claimed in claim 1, wherein the processing unit is further adapted to process the received ultrasound data so as to derive one or more hemodynamic parameters of the heart.

13. An ultrasound processing method, comprising:
receiving ultrasound data representative of an anatomical region of interest over a period of time;
processing the data to identify a particular anatomical feature within the data;
performing an alignment check procedure, the procedure comprising determining whether an alignment of the anatomical feature within a field of view of the ultrasound transducer unit is changing over time, wherein alignment of the anatomical feature within a field of view of the ultrasound transducer unit comprises a determined distance between the anatomical feature and a border of the field of view, and wherein determining whether the alignment of the anatomical feature within the field of view of the ultrasound transducer unit is changing over time comprises determining a change in the determined distance between the anatomical feature and the border of the field of view over time; and
in response to determining that the alignment is changing, generating an output signal for communicating said determination to a user, and
determining an estimated time duration until the alignment of the anatomical feature will move outside of a set of one or more defined limits and generating an information output representative of said time duration, wherein the estimated time duration is an estimated future time duration until the alignment of the anatomical feature will move outside of the field of view of the ultrasound transducer unit.

14. The method as claimed in claim 13, wherein the alignment check procedure further comprises deriving, based on any detected changes in alignment, a corresponding speed of movement of the anatomical feature within the field of view represented by the changes.

* * * * *